(12) United States Patent
Lin

(10) Patent No.: US 6,227,358 B1
(45) Date of Patent: May 8, 2001

(54) CONDOM STORING BOX

(76) Inventor: Chiou-Lan Lin, 3F, No. 18, Szu-Wei Road, Taipei City (TW)

( * ) Notice: Subject to any disclaimer, the term of this patent is extended or adjusted under 35 U.S.C. 154(b) by 0 days.

(21) Appl. No.: 09/454,215

(22) Filed: Dec. 9, 1999

(51) Int. Cl.[7] ................................................. B65D 85/14
(52) U.S. Cl. ............................................................ 206/69
(58) Field of Search .............................. 206/69, 232, 581, 206/457, 37, 38

(56) References Cited

U.S. PATENT DOCUMENTS

| | | | |
|---|---|---|---|
| 1,623,994 | * 4/1927 | Buchsbaum et al. | |
| 1,861,644 | * 6/1932 | Roberts | |
| 5,056,660 | * 10/1991 | Huang | 206/232 |
| 5,170,887 | * 12/1992 | Potts et al. | 206/69 |
| 5,299,434 | * 4/1994 | Kaufman | 206/69 |
| 5,316,019 | * 5/1994 | Jones | 206/69 |
| 5,427,233 | * 6/1995 | Zinck et al. | 206/69 |
| 5,697,127 | * 12/1997 | Tyler | 206/69 |
| 5,740,814 | * 4/1998 | Comi | 128/844 |
| 5,862,908 | * 1/1999 | Arbin | 206/69 |
| 5,996,832 | * 12/1999 | Nieuwoudt | 206/270 |

* cited by examiner

*Primary Examiner*—David T. Fidei

(57) ABSTRACT

A condom storing box includes a curved upper part and a substantially flat bottom part. The bottom part has a convex edge ring for connecting the brim of the upper part. A tightly sealed space is formed between the upper and bottom parts for storing condoms. An opening system is fastened to the bottom part for easily breaking and opening the bottom part of the box. A bottom cover is also provided to cover up the opening system and the bottom part. The bottom cover can also be used to mount or affix a supporting or fixing device so that the condom storing box can be worn or attached as a decorative accessory.

1 Claim, 5 Drawing Sheets

CONDOM STORING BOX

FIELD OF THE INVENTION

The present invention relates to a condom storing box, and more specifically, to a container with a closed structure to secretly store a plurality of condoms.

BACKGROUND OF THE INVENTION

Condom is a product that requires special advertisement and selling because it relates to intimate personal behavior and easily makes people somewhat embarrassed even when mentioning it.

Although the purpose of the condom is very apparent and the sex concept in the society is more open than the old days, it is still difficult to sell condoms simply by the way other common daily products are sold.

Due to the above mental obstacles, and some concerns about the specification in the sanitation and safety, the package of the condom should meet some incompatible requirements in selling condition.

SUMMARY OF THE INVENTION

An object of the present invention is to provide a storing box with special outlook and package, which successfully incorporates several incompatible requirements to overcome the obstacle in the market for the condom. The primary feature of the invention is that the condom storing box comprises a first surface and a second surface, which are opposite to each other. The first surface is a plane bottom used to firmly place the condom container. The second surface is a convex surface designed to store internal matters. Any type of known opening system can be installed on said first surface.

It is also an object of the invention to provide a structure that can be used to store condom in a tightly sealed space. According to the present invention, the condom storing box comprises an upper part and a bottom part. The upper part has a curved surface joined with a cylindrical brim. The bottom part has a convex edge ring that tightly clamps the cylindrical brim to form a tightly sealed space between the upper and bottom parts for storing condoms.

Another object of the invention is to provide an opening system that can be safely used to open the condom storing box without damaging the condoms. Accordingly, the opening system includes a prying plate affixed to the bottom part of the condom storing box by a fastener. The prying plate has a ring to be held by a finger for prying and breaking the bottom part through a brittle ring formed on the bottom part.

Yet another object of the invention is to provide a bottom cover for covering up the opening system and the bottom part of the condom storing box. In addition, a supporting device or a fixing device can be mounted or affixed on the bottom cover in such a way that the condom storing box can be worn or attached as a decorative accessory.

Other features and advantages of the invention will become apparent from the following description of the invention which refers to the accompanying drawings.

DETAILED DESCRIPTION OF THE PREFERRED EMBODIMENTS

Figure 1:
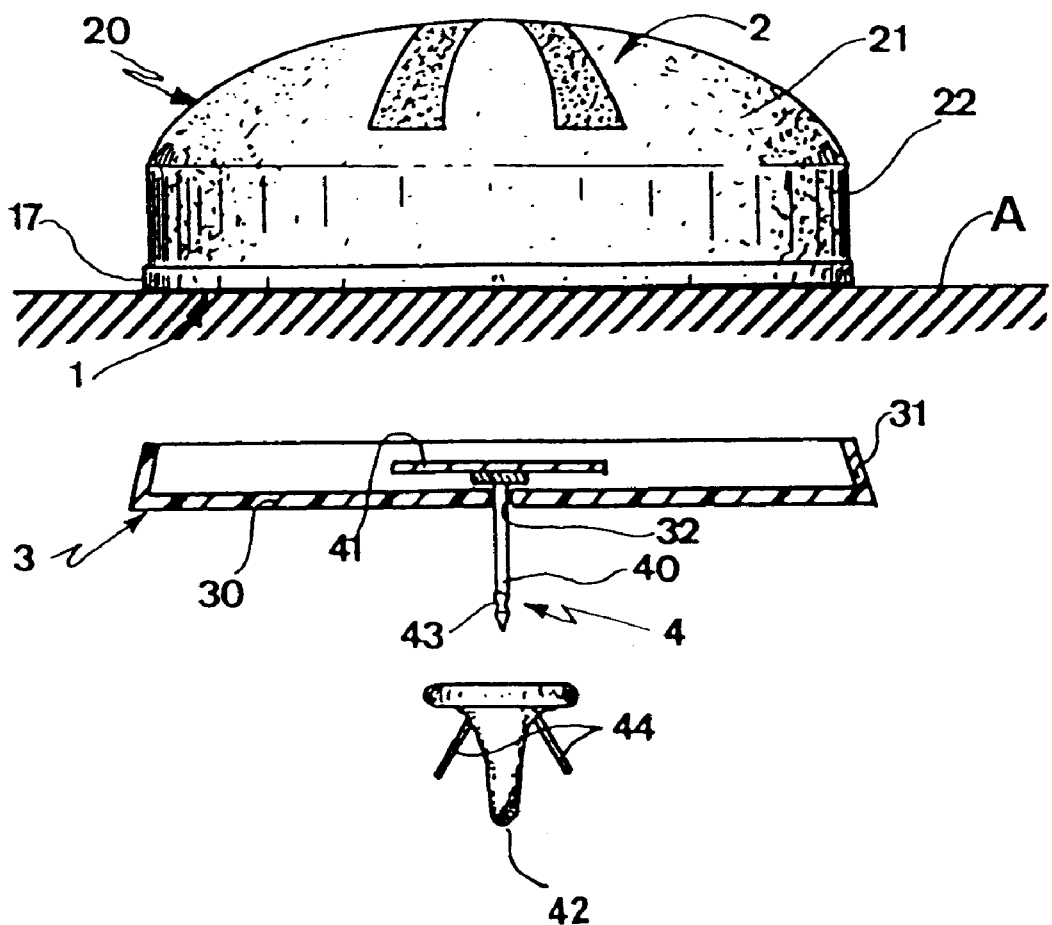
FIG. 1 is a schematic diagram of the condom storing box placed on a plane according to the present invention, illustrating the sealed cover and the brooch.

With reference to FIG. 1, there are two opposite surfaces in the condom storing box, including a first surface 1 and a second surface 2.

The first surface 1 is basically flat so as to be firmly placed on the plane A, such as a table.

The second surface 2, on the contrary, has a convex round shape, as shown in FIG. 1. Thus, if the condom storing box is placed with the second surface 2 on the plane A, it is easily found that the box is not firmly placed. This indicates a wrong way to place the box.

The second surface 2 has a function of reminding the user of correctly placing the flat surface on the plane.

Figure 2:
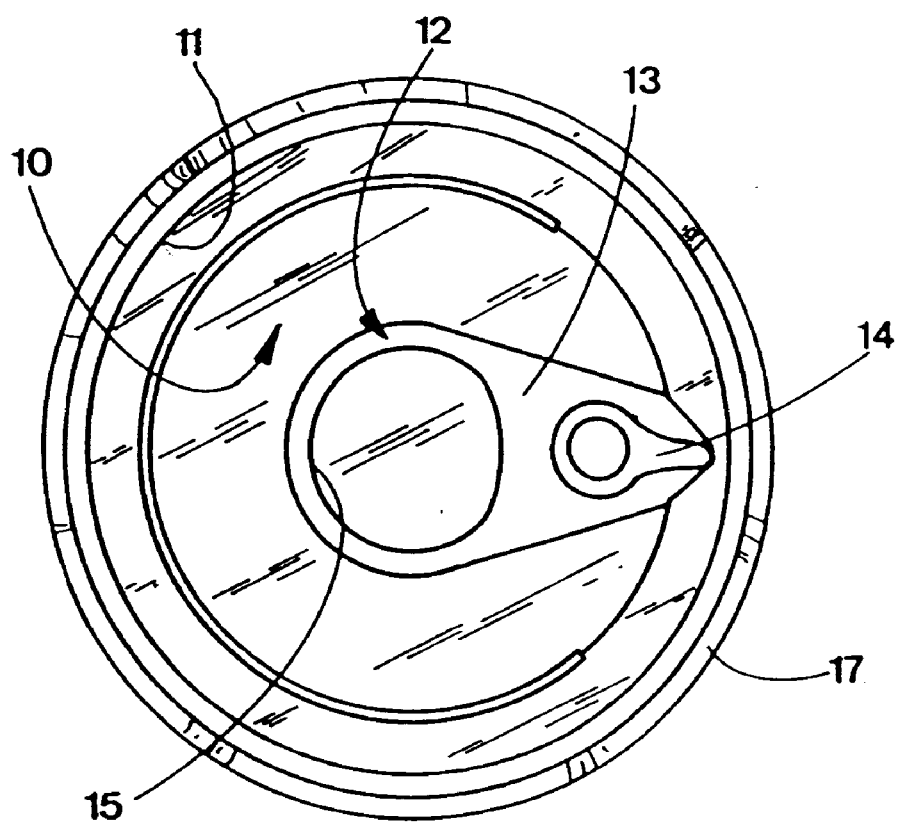
FIG. 2 is a bottom view of the condom storing box in FIG. 1.

According to the invention, the condom storing box comprises an upper part 20 as can be seen in FIG. 1 and a bottom part 10 as illustrated in FIG. 2. The bottom part has a brittle ring 11. Both upper and bottom parts are usually made of metal. An opening system is affixed to the bottom part 10 as shown in FIG. 2.

The opening system comprises a prying plate 12, which is fixed on the bottom part 10 by a fastener 13 near an end 14. The prying plate 12 has a ring 15 as large as a finger.

The prying plate 12 tightly contacts with the bottom part 10 and is protruded out of the bottom part 10. Therefore, the prying plate 12 will cause the box to be unstable if the box is directly placed on the plane A.

Figure 4:
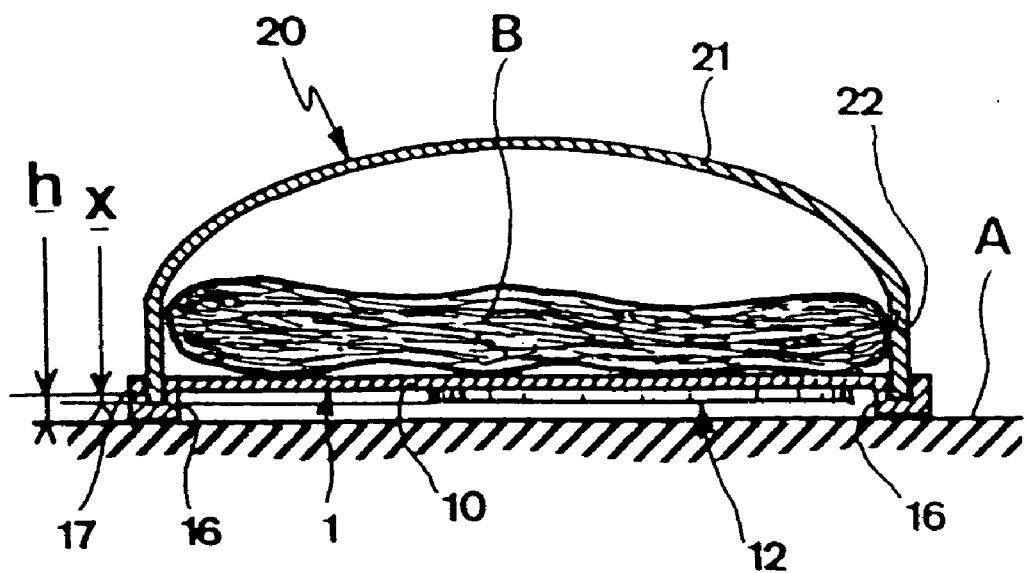
FIG. 4 is a sectional view of the condom storing box in FIG. 1.

To firmly place the box, the bottom part 10 is formed with ring with a round shape and a height not less than the height x of the prying plate 12 as shown in FIG. 4. The convex edge ring should also surround a the prying plate such that the convex edge ring forms a stable bottom to well contact with the plane A.

The upper part 20 comprises a curved surface 21 joined with a cylindrical brim 22 which connected to the bottom part 10 through the convex edge ring 16. The connection is made by inserting the cylindrical brim 22 into the convex edge ring 16 and bending the curved side 17 of the convex edge ring 16 towards the cylindrical brim 22. After condoms are placed between the upper and bottom parts, the condom storing box is sealed by pressing the bent and curved edge ring 16 to tightly connect the upper and lower parts.

Figure 3:
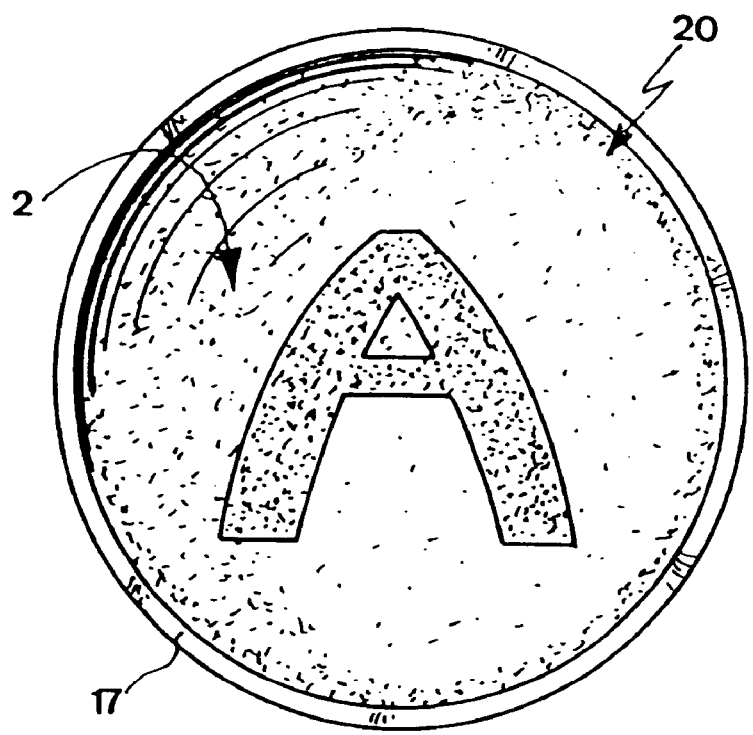
FIG. 3 is a top view of the condom storing box in FIG. 1.

To enhance the function of the upper part 20 for reminding the user to correctly place the storing box, some decorated stripes or characters (such as alphabet A) can be painted or printed on the outer surface of the upper part 20, as shown in FIG. 3.

For example, the decorated stripes on the upper part 20 may refer to some advertising pattern with more contrast color painted or printed on the curved surface 21 and the cylindrical brim 22, which are both in a single color.

The curved side 17 keeps the original color of the bottom part 10. Accordingly, the contrast effect of the upper part 20 and the bottom part 10 are strengthened and it is apparent that the storing box has a sealed cover, which covers a metal body.

The rigid feature of the storing box comes from the material to provide sufficient protective force against the pressing force applied.

The condoms stored within the storing box is protected by such rigidity and sealing property to meet the most strict specification and requirement.

Therefore, both packaged and unpackaged condoms B may be stored within the storing box, which is vacuum or has the content of air under control.

The storing box has a beautiful looking due to such special shape and decorated stripes so that the purpose of storing the condoms is not easily associated with.

Additionally, the opening system is hidden, so the storing box looks like a common box containing candies, pills, or oral medicine.

FIG. 1 illustrates an embodiment by adding an additional bottom cover 30 to completely hide the opening system. The bottom cover 30 made of plastic may have a flat bottom and the diameter is greater than the curved side 17. The brim side 31 is included in the bottom cover 30. The bottom 3 can be easily shipped onto the bottom part of the storing box because the brim side 31 tightly sleeves the outer of the curved side 17 by elastic deformation within the allowable limitation.

The brim side 31 is somewhat oblique towards the center so as to naturally and tightly sleeve the storing box by the property of the material and structure.

The storing box has a special feature that the opening system is invisible even if the storing box is placed upside down.

The storing box can easily become another matter like clothes or bag accessory to carry simply by adding a supporting device or a fixing device, such as a magnet or sticky piece.

A brooch 4 is an example of the fixing device, which is formed by a pin 40 fixed on a base plate 41 penetrating through the central hole 32 of the bottom 3.

Furthermore, the pin 40 penetrates through the textile of clothes, a scarf, a bag or a knapsack, and then enclosed by a cap 42.

A clamp with two jaws is included in the cap 42 (not shown) The pin 40 is inserted into the clamp and has a round slot 43 to prevent the pin 40 from slipping with respect to the cap 42.

When enclosed by the cap 42, the pin 40 can be released by pressing two fins 44 on the cap 42 and clamped again by releasing the two fins 44 so that the round slot 43 is held by the clamp.

The opening system should be designed as simple as possible to prevent the condoms from damage.

Figure 5:
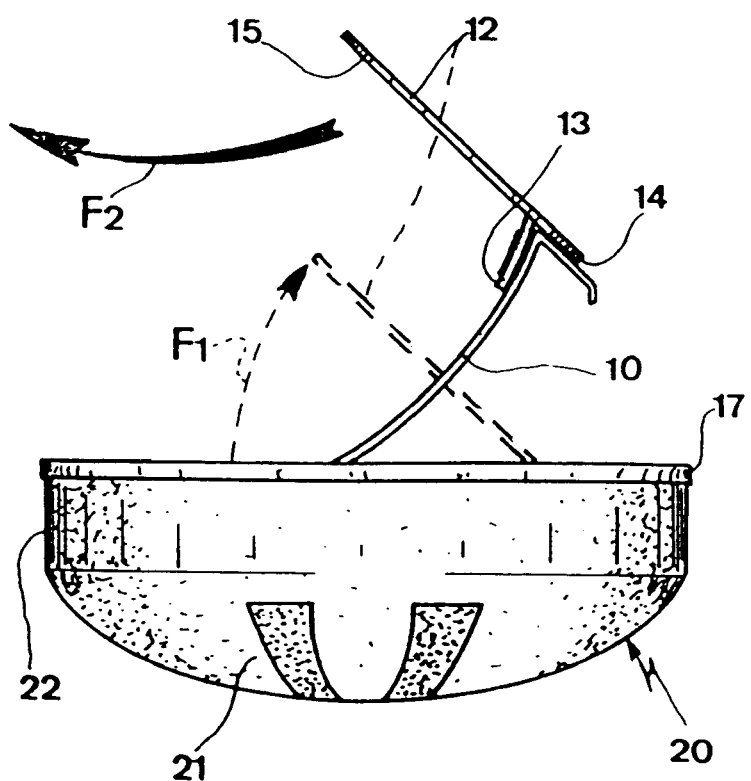
FIG. 5 is a sectional view of the condom storing box in FIG. 1 when opened.

FIG. 5 shows that the user should first pull up the prying plate along the direction of arrow F1 to generate two effects: first, the end of the prying plate will escape from the bottom part 10 for the ring 15 to hold; second, another end 14 of the prying plate greatly presses the bottom part 10 to locally collapse downwards along the brittle ring 11 and further easily cause continuously breaking.

Moreover, the user puts one finger within the ring 15 and then lightly pulls up along the direction of arrow F2 such that the brittle ring 11 is caused to break along the convex edge ring 16. That is, the bottom part 10 will be completely released without any residue except the convex edgering 16.

Therefore, the condoms B can be easily fetched without any force to cause damage, including pulling, twisting, or clamping. Additionally, the opening system does not include any sharp piece, so the condoms have no risk of suffering damage.

As long as the storing box are not opened, the condoms is very safe without suffering common deterioration, such as breaking, stinging during or after packaging, pollution, squashing, or burning down.

The internal of the storing box is completely isolated from the external environment because the metal structure and the closed property.

Although the above storing box is described to be made of metal, the present invention may use other material, especially synthetic. material. However, it should be noted that the condoms need to be kept in a sterilized state, so the outer case of the storing box is prevented from penetrating. Meanwhile, to prevent the bacteria, no gap is allowed even if it is a tiny gap which is visible only by a microscope.

Although only the preferred embodiments of this invention were shown and described in the above description, it is requested that any modification or combination that comes within the spirit of this invention be protected.

What is claimed is:

1. A condom storing box comprising:
    an upper part having a curved surface and a cylindrical brim joined together;
    a bottom part having a brittle ring formed thereon and a convex edge ring, said convex edge ring tightly clamping said cylindrical brim for connecting said bottom and upper parts and to form a sealed space for storing condoms;
    an opening system affixed to said bottom part, said opening system comprising a prying plate having a first end with a ring formed thereon and a second end fastened to said bottom part by a fastener;
    a bottom cover slipped onto said convex edge ring for covering said bottom part and said opening system, said bottom cover having a center hole; and
    a fixing device including a pin formed on a base plate and a fixing cap having clamps;
    wherein said base plate is positioned between said bottom part and said bottom cover, said pin passes through said bottom cover, and said fixing cap clamps said pin.

* * * * *